(12) United States Patent
Boukhny et al.

(10) Patent No.: US 8,808,308 B2
(45) Date of Patent: *Aug. 19, 2014

(54) AUTOMATED INTRAOCULAR LENS INJECTOR DEVICE

(75) Inventors: Mikhail Boukhny, Laguna Niguel, CA (US); Bill Chen, Irvine, CA (US); James Chon, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 296 days.

This patent is subject to a terminal disclaimer.

(21) Appl. No.: 13/360,099

(22) Filed: Jan. 27, 2012

(65) Prior Publication Data

US 2013/0197531 A1 Aug. 1, 2013

Related U.S. Application Data

(63) Continuation of application No. 12/249,996, filed on Oct. 13, 2008, now Pat. No. 8,308,736.

(51) Int. Cl.
*A61F 2/16* (2006.01)
*A61F 9/00* (2006.01)

(52) U.S. Cl.
USPC .......................................... 606/107; 623/6.12

(58) Field of Classification Search
CPC ... A61F 2/1662; A61F 2/1664; A61F 2/1667; A61F 2/167; A61F 2/1672; A61F 2/1678; A61F 2/1691
USPC ........................... 606/107; 623/4.1, 6.11, 6.12
See application file for complete search history.

(56) References Cited

U.S. PATENT DOCUMENTS

| 4,573,998 | A | 3/1986 | Mazzocco |
| 4,619,657 | A | 10/1986 | Keates et al. |
| 4,681,102 | A | 7/1987 | Bartell |
| 4,747,404 | A | 5/1988 | Jampel et al. |
| 4,834,094 | A | 5/1989 | Patton et al. |
| 4,836,201 | A | 6/1989 | Patton et al. |
| 4,919,130 | A | 4/1990 | Stoy et al. |
| 4,934,363 | A | 6/1990 | Smith et al. |

(Continued)

FOREIGN PATENT DOCUMENTS

| AU | 728443 | 1/2001 |
| DE | 4301573 | 7/1994 |

(Continued)

OTHER PUBLICATIONS

International Search Report for PCT/US2012/030147, Publication No. WO2012/129419, dated Jul. 13, 2010, 2 pages.

(Continued)

*Primary Examiner* — Ryan Severson
(74) *Attorney, Agent, or Firm* — Darien Reddick

(57) ABSTRACT

An intraocular lens injection device comprises a tubular housing with a plunger longitudinally disposed within the tubular housing. An electric drive system longitudinally translates the plunger so that its tip engages an insertion cartridge to fold and displace an intraocular lens disposed within and to inject the folded lens into the lens capsule of an eye. A control circuit is configured to start translation of the plunger, responsive to user input, to detect at least one fault condition based on a counter-electromotive force produced by the electric motor, and to stop translation of the plunger assembly responsive to the detected fault condition, which may comprise excessive resistance to forward or rearward translation of the plunger or insufficient resistance to forward translation of the plunger.

21 Claims, 11 Drawing Sheets

(56) References Cited

U.S. PATENT DOCUMENTS

| | | |
|---|---|---|
| 4,960,557 A | 10/1990 | Sorensen |
| 5,007,913 A | 4/1991 | Dulebohn et al. |
| 5,026,396 A | 6/1991 | Darin |
| 5,098,439 A | 3/1992 | Hill et al. |
| 5,190,552 A | 3/1993 | Kelman |
| 5,275,604 A | 1/1994 | Rheinish et al. |
| 5,304,182 A | 4/1994 | Rheinish et al. |
| 5,354,333 A | 10/1994 | Kammann et al. |
| 5,397,313 A | 3/1995 | Gross |
| 5,425,734 A | 6/1995 | Blake |
| 5,444,183 A | 8/1995 | Gehrs et al. |
| 5,464,396 A | 11/1995 | Barta et al. |
| 5,468,246 A | 11/1995 | Blake |
| 5,494,484 A | 2/1996 | Feingold |
| 5,496,278 A | 3/1996 | Buff |
| 5,496,328 A | 3/1996 | Nakajima et al. |
| 5,499,987 A | 3/1996 | Feingold |
| 5,578,042 A | 11/1996 | Cumming |
| 5,582,614 A | 12/1996 | Feingold |
| 5,607,433 A | 3/1997 | Polla et al. |
| 5,616,148 A | 4/1997 | Eagles et al. |
| 5,620,450 A | 4/1997 | Eagles et al. |
| 5,629,577 A | 5/1997 | Polla et al. |
| 5,643,275 A | 7/1997 | Blake |
| 5,643,276 A | 7/1997 | Zaleski |
| 5,653,715 A | 8/1997 | Reich et al. |
| 5,653,753 A | 8/1997 | Brady et al. |
| 5,716,364 A | 2/1998 | Makker et al. |
| 5,728,102 A | 3/1998 | Feingold et al. |
| 5,735,858 A | 4/1998 | Makker et al. |
| 5,772,666 A | 6/1998 | Feingold et al. |
| 5,776,138 A | 7/1998 | Vidal et al. |
| 5,800,441 A | 9/1998 | Polla et al. |
| 5,800,442 A | 9/1998 | Wolf et al. |
| 5,803,925 A | 9/1998 | Yang et al. |
| 5,810,834 A | 9/1998 | Heyman |
| 5,820,373 A | 10/1998 | Okano et al. |
| 5,860,986 A | 1/1999 | Reich et al. |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,891,153 A | 4/1999 | Peterson |
| 5,944,725 A | 8/1999 | Cicenas et al. |
| 5,947,976 A | 9/1999 | Van Noy et al. |
| 6,010,510 A | 1/2000 | Brown et al. |
| 6,042,587 A | 3/2000 | Polla et al. |
| 6,056,757 A | 5/2000 | Feingold |
| 6,056,758 A | 5/2000 | Vidal et al. |
| 6,083,231 A | 7/2000 | Van Noy et al. |
| 6,140,602 A | 10/2000 | Costin |
| 6,143,001 A | 11/2000 | Brown et al. |
| 6,162,229 A | 12/2000 | Feingold et al. |
| 6,162,230 A | 12/2000 | Polla et al. |
| 6,163,963 A | 12/2000 | Huang |
| 6,179,843 B1 | 1/2001 | Weiler |
| 6,228,094 B1 | 5/2001 | Erdman |
| 6,254,607 B1 | 7/2001 | Makker et al. |
| 6,276,014 B1 | 8/2001 | Lee |
| 6,334,862 B1 | 1/2002 | Vidal et al. |
| 6,355,046 B2 | 3/2002 | Kikuchi et al. |
| 6,423,035 B1 | 7/2002 | Das et al. |
| 6,447,519 B1 | 9/2002 | Brady et al. |
| 6,471,708 B2 | 10/2002 | Green |
| 6,497,708 B1 | 12/2002 | Cumming |
| 6,500,181 B1 | 12/2002 | Portney |
| 6,503,275 B1 | 1/2003 | Cumming |
| 6,558,395 B2 | 5/2003 | Hjertman et al. |
| 6,592,591 B2 | 7/2003 | Polla et al. |
| 6,607,537 B1 | 8/2003 | Binder |
| 6,635,731 B2 | 10/2003 | Mentak |
| 6,666,871 B2 | 12/2003 | Kikuchi et al. |
| 6,685,740 B2 | 2/2004 | Figueroa et al. |
| 6,887,221 B1 | 5/2005 | Baillargeon et al. |
| 6,899,717 B2 | 5/2005 | Weber et al. |
| 6,923,815 B2 | 8/2005 | Brady et al. |
| 6,964,648 B2 | 11/2005 | Talling et al. |
| 6,976,989 B1 | 12/2005 | Vincent |
| 7,014,641 B2 | 3/2006 | Kobayshi et al. |
| 7,042,180 B2 | 5/2006 | Terry et al. |
| 7,097,649 B2 | 8/2006 | Meyer |
| 7,131,976 B2 | 11/2006 | Kobayaski et al. |
| 7,156,854 B2 | 1/2007 | Brown et al. |
| 7,156,855 B2 | 1/2007 | Oda |
| 7,189,218 B2 | 3/2007 | Lichtenberg |
| 7,279,006 B2 | 10/2007 | Vincent |
| 7,422,604 B2 | 9/2008 | Vaquero et al. |
| 7,429,263 B2 | 9/2008 | Vaquero et al. |
| 8,109,938 B2 | 2/2012 | Pessin |
| 2001/0007075 A1 | 7/2001 | Hjertman et al. |
| 2002/0022881 A1 | 2/2002 | Figueroa et al. |
| 2003/0040755 A1 | 2/2003 | Meyer |
| 2003/0135221 A1 | 7/2003 | Sabet |
| 2003/0139749 A1 | 7/2003 | Kikuchi et al. |
| 2003/0212406 A1 | 11/2003 | Kobayashi et al. |
| 2003/0212409 A1 | 11/2003 | Kobayashi et al. |
| 2004/0054374 A1 | 3/2004 | Weber et al. |
| 2004/0059343 A1 | 3/2004 | Shearer et al. |
| 2004/0087896 A1 | 5/2004 | Wise et al. |
| 2004/0097956 A1 | 5/2004 | Oda |
| 2004/0127911 A1 | 7/2004 | Figueroa et al. |
| 2004/0147938 A1 | 7/2004 | Dusek et al. |
| 2004/0160575 A1 | 8/2004 | Ayton et al. |
| 2004/0199174 A1 | 10/2004 | Herberger et al. |
| 2004/0215207 A1 | 10/2004 | Cumming |
| 2004/0238392 A1 | 12/2004 | Peterson et al. |
| 2005/0029976 A1 | 2/2005 | Terry et al. |
| 2005/0049605 A1 | 3/2005 | Vaquero et al. |
| 2005/0049606 A1 | 3/2005 | Vaquero et al. |
| 2005/0065534 A1 | 3/2005 | Hohl |
| 2005/0143750 A1 | 6/2005 | Vaquero |
| 2005/0149056 A1 | 7/2005 | Rathert |
| 2005/0149057 A1 | 7/2005 | Rathert |
| 2005/0203619 A1 | 9/2005 | Altmann |
| 2005/0222578 A1 | 10/2005 | Vaquero |
| 2005/0222579 A1 | 10/2005 | Vaquero et al. |
| 2006/0063962 A1 | 3/2006 | Drobnik et al. |
| 2006/0085013 A1 | 4/2006 | Dusek et al. |
| 2006/0167466 A1 | 7/2006 | Dusek |
| 2006/0184181 A1 | 8/2006 | Cole et al. |
| 2006/0200167 A1 | 9/2006 | Peterson et al. |
| 2006/0229633 A1 | 10/2006 | Shepherd |
| 2006/0229634 A1 | 10/2006 | Shepherd |
| 2006/0235429 A1 | 10/2006 | Lee et al. |
| 2006/0284581 A1 | 12/2006 | Mullin et al. |
| 2007/0005135 A1 | 1/2007 | Makker et al. |
| 2007/0050023 A1 | 3/2007 | Bessiere et al. |
| 2007/0060925 A1 | 3/2007 | Pynson |
| 2007/0150056 A1 | 6/2007 | Meyer |
| 2007/0173860 A1 | 7/2007 | Iwaski |
| 2008/0033449 A1 | 2/2008 | Cole et al. |
| 2008/0039862 A1 | 2/2008 | Tran |
| 2008/0058830 A1 | 3/2008 | Cole et al. |
| 2008/0097459 A1 | 4/2008 | Kammerlander et al. |
| 2008/0119865 A1 | 5/2008 | Meunier et al. |
| 2008/0200920 A1 | 8/2008 | Downer |
| 2008/0200921 A1 | 8/2008 | Downer |
| 2008/0221584 A1 | 9/2008 | Downer |
| 2008/0221585 A1 | 9/2008 | Downer |
| 2008/0255577 A1 | 10/2008 | Downer |
| 2009/0043313 A1 | 2/2009 | Ichinohe et al. |
| 2009/0112223 A1 | 4/2009 | Downer |
| 2009/0171366 A1 | 7/2009 | Tanaka |
| 2009/0204123 A1 | 8/2009 | Downer |
| 2009/0216244 A1 | 8/2009 | Pynson |
| 2010/0094309 A1 | 4/2010 | Boukhny et al. |
| 2010/0121340 A1 | 5/2010 | Downer |

FOREIGN PATENT DOCUMENTS

| | | |
|---|---|---|
| EP | 0174917 | 3/1986 |
| EP | 0 270 257 | 6/1988 |
| EP | 0 363 213 | 4/1990 |
| EP | 0477466 | 6/1996 |

(56) References Cited

FOREIGN PATENT DOCUMENTS

| | | |
|---|---|---|
| EP | 0820211 | 1/1998 |
| EP | 0 858 304 | 8/1998 |
| EP | 0962195 | 12/1999 |
| EP | 1 011 561 | 6/2000 |
| EP | 1 076 408 | 2/2001 |
| EP | 1 332 731 A1 | 8/2003 |
| EP | 1 332 731 B1 | 8/2003 |
| EP | 1360944 | 11/2003 |
| EP | 1481652 | 12/2004 |
| EP | 1661533 | 5/2006 |
| EP | 1832247 | 9/2007 |
| EP | 1849436 A1 | 10/2007 |
| EP | 1891911 | 2/2008 |
| EP | 1958593 | 8/2008 |
| EP | 2062552 | 5/2009 |
| FR | 2820633 | 8/2002 |
| GB | 2 224 214 | 5/1990 |
| JP | 1176288 | 12/1989 |
| JP | H09-506285 | 2/1996 |
| JP | 10309294 | 11/1998 |
| JP | 10511876 | 11/1998 |
| JP | 10512460 | 11/1998 |
| JP | 2000025073 | 1/2000 |
| JP | 2000513955 | 10/2000 |
| JP | 2003048488 | 2/2003 |
| JP | 2003070829 | 3/2003 |
| JP | 2003325569 | 11/2003 |
| JP | 2006006817 | 1/2006 |
| JP | 2006014962 | 1/2006 |
| JP | 2006181269 | 7/2006 |
| JP | 2007055057 | 3/2007 |
| JP | 2007-215990 | 8/2007 |
| RU | 2138232 | 9/1999 |
| RU | 2171100 | 7/2001 |
| RU | 2238283 | 10/2004 |
| RU | 2242956 | 12/2004 |
| SU | 1440496 | 11/1988 |
| WO | WO 94/07436 A1 | 4/1994 |
| WO | WO 94/20027 | 9/1994 |
| WO | WO 96/10372 | 4/1996 |
| WO | WO 96/20662 | 7/1996 |
| WO | WO 96/28122 | 9/1996 |
| WO | 9629956 | 10/1996 |
| WO | WO 96/29956 | 10/1996 |
| WO | WO 97/15253 | 5/1997 |
| WO | WO 97/26841 | 7/1997 |
| WO | WO 98/05281 | 2/1998 |
| WO | WO 98/12969 | 4/1998 |
| WO | WO 98/15244 | 4/1998 |
| WO | WO 98/20819 | 5/1998 |
| WO | WO 00/40175 | 7/2000 |
| WO | WO 00/62712 | 10/2000 |
| WO | WO 2004/091447 | 10/2004 |
| WO | WO 2005/018515 | 3/2005 |
| WO | WO 2005/020853 | 3/2005 |
| WO | WO 2005/023154 A2 | 3/2005 |
| WO | WO 2005/023154 A3 | 3/2005 |
| WO | WO 2005/102223 | 11/2005 |
| WO | WO 2006/059183 | 6/2006 |
| WO | 2006/070628 | 7/2006 |
| WO | WO 2006/070561 | 7/2006 |
| WO | WO 2006/080191 | 8/2006 |
| WO | WO 2006/113138 | 10/2006 |
| WO | WO 2006/113357 | 10/2006 |
| WO | 2007054645 | 5/2007 |

OTHER PUBLICATIONS

International Search Report for PCT/US2010/023544, Publication No. WO2010/093593, dated May 28, 2010, 4 pages.
PCT International Preliminary Report on Patentability and Written Opinion, PCT/US2010/023544, dated Aug. 16, 2011, 4 pages.
International Search Report for PCT/US2011/032708, Publication No. WO2011/133427, dated Jun. 29, 2011, 2 pages.
Written Opinion of the International Searching Authority, International Application No. PCT/US2011/032708, dated Jun. 29, 2011, 4 pages.
European Search Report for Application No. 07114085.9, Publication No. EP1891911, dated Jan. 14, 2008, 2 pages.
European Search Report for Application No. 08100876.5, Publication No. EP1958593, dated Apr. 22, 2008, 2 pages.
European Search Report for Application No. 09154535.0, Publication No. EP2062552, dated Apr. 15, 2009, 2 pages.
International Search Report for PCT/US2009/057,083, Filed Sep. 16, 2009, Publication No. WO2010/044,974, Published Apr. 22, 2010, 5 pages.
Abstract of article entitled "Implantation of the AcrySof MA30BA lens using the Monarch System" by Barakova D., original article found in Cesk slov Oftalmol, 2002 58(3), at p. 149-152, found in PubMed database at http://www.ncbi.nlm.nih.gov/pubmed/12087658 (1 page).
International Preliminary Report on Patentability with Written Opinion, dated Apr. 19, 2011, Application No. PCT/US2009/057083, Filed Sep. 16, 2009, Publication No. WO2010/044,974, Published Apr. 22, 2010, 7 pages.
European Search Report for Application No. 08102172.7, Publication No. 1980219, dated Oct. 15, 2008, 5 pages.
Extended European Search Report for Application No. 11772480.7, Publication No. EP2528561, dated Oct. 2, 2013, 5 pages.
PCT International Preliminary Report on Patentability and Written Opinion, PCT/US2012/030147, filed Mar. 22, 2012, Publication No. 2012/129,419, Published Sep. 27, 2012, dated Sep. 24, 2013, 9 pages.
Shao; "Direct Back EMF Detection Method for Sensorless Brushless DC (BLDC) Motor Drives"; Virginia Polytechnic Institute and State University, Blacksburg, Virginia; Sep. 2003 (http://scholar.lib.vt.edu/theses/available/etd-09152003-171904/unrestricted/T.pdf); 91 pages.

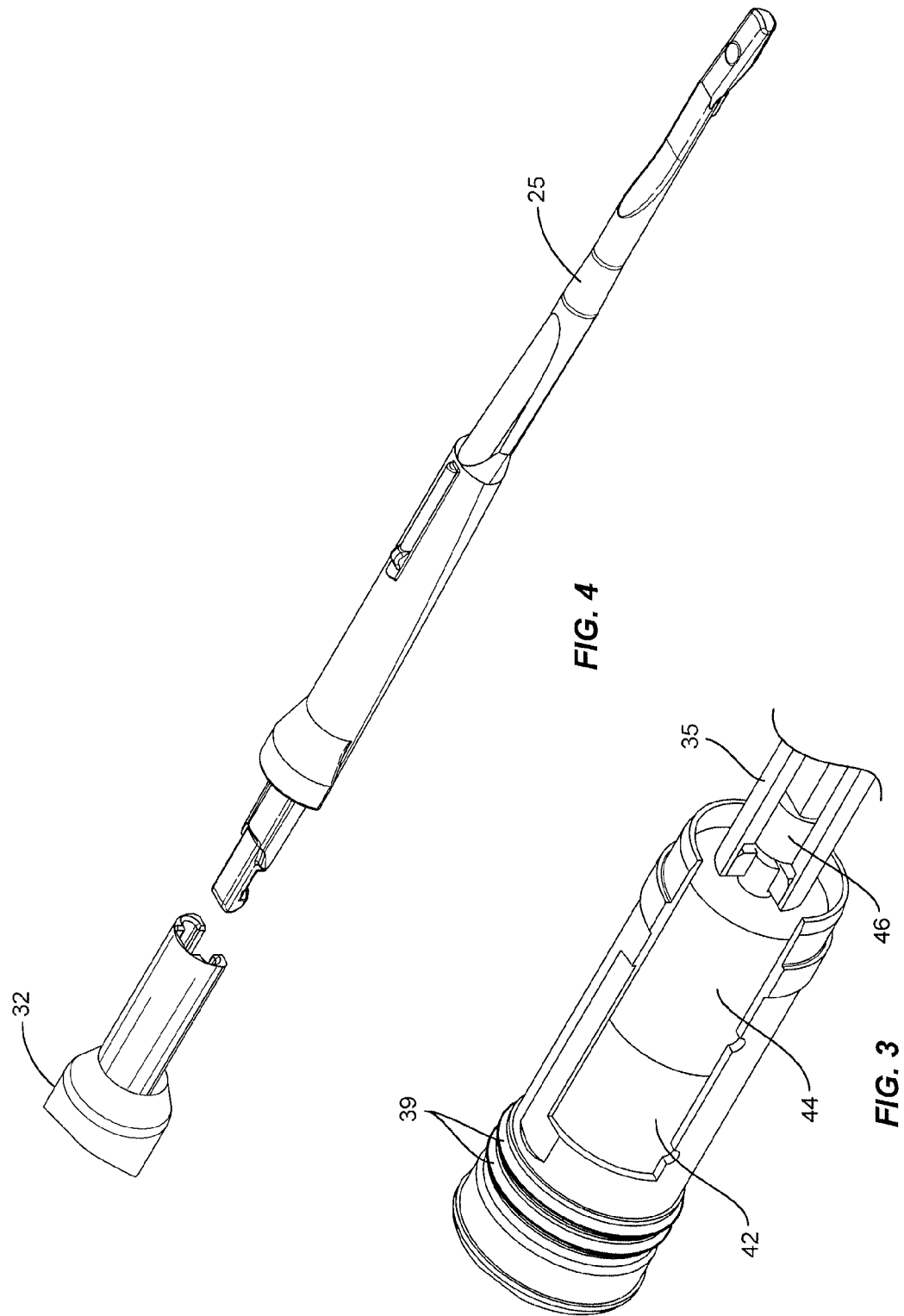

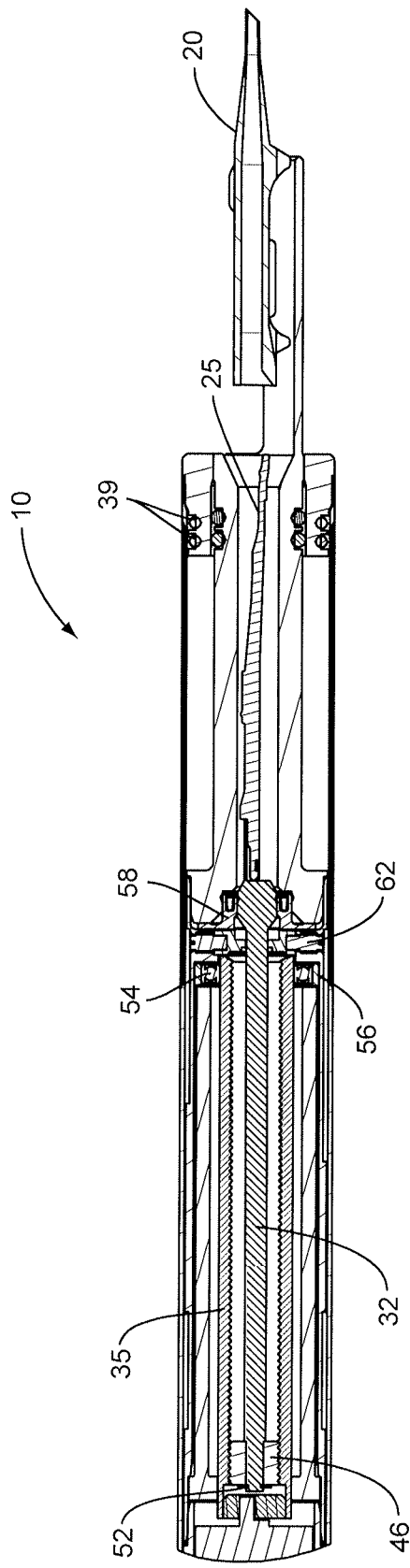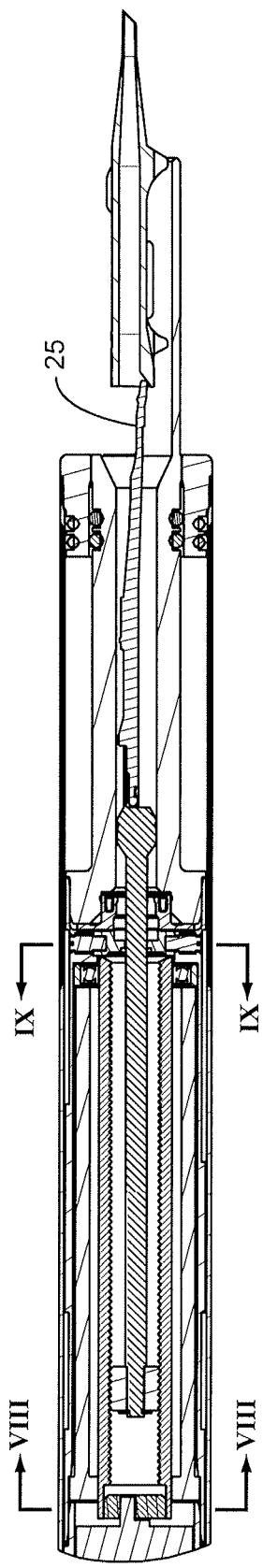
FIG. 6
FIG. 7

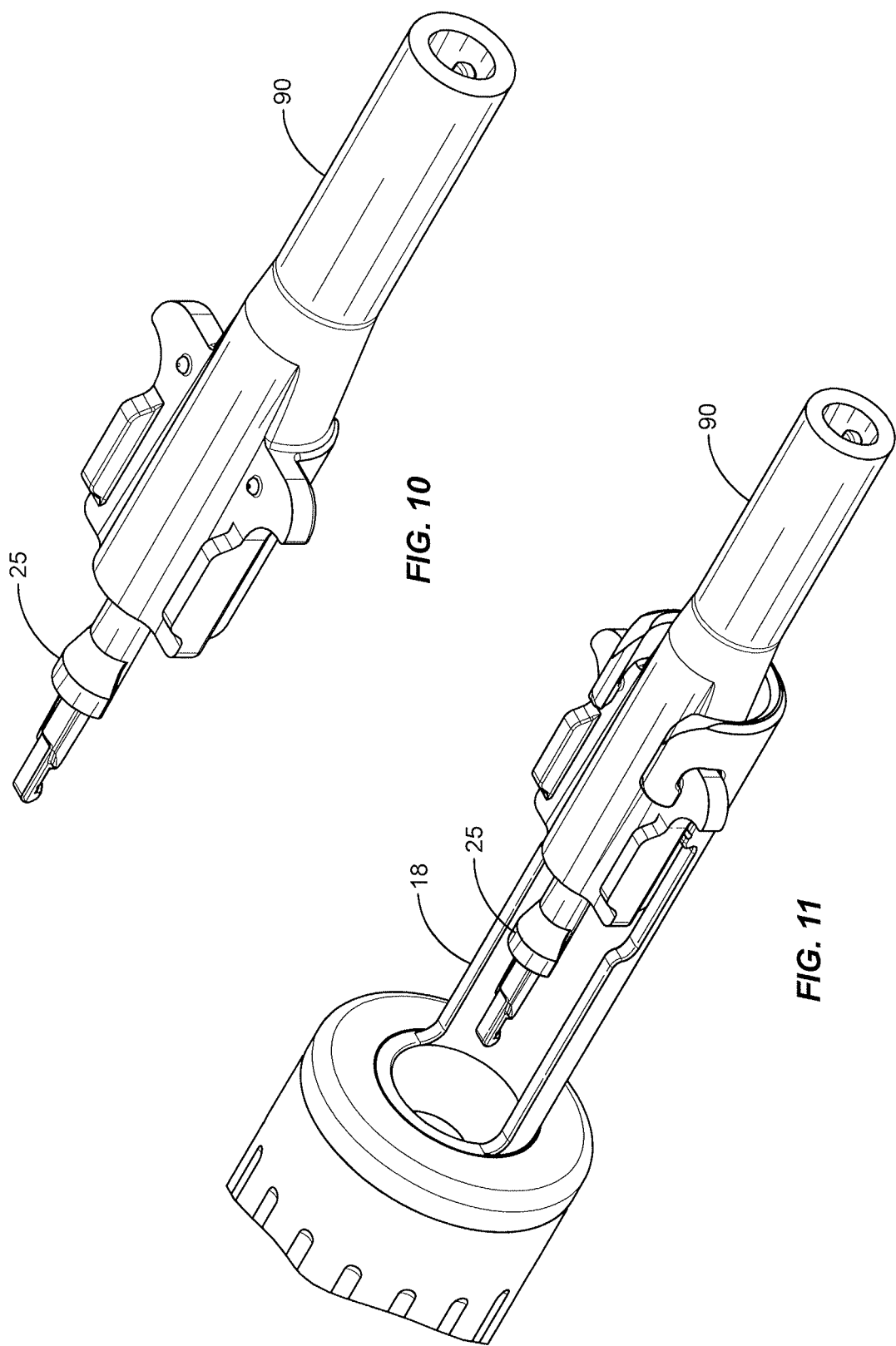

AUTOMATED INTRAOCULAR LENS INJECTOR DEVICE

CROSS REFERENCE TO RELATED APPLICATIONS

This application is a continuation application of prior application Ser. No. 12/249,996, filed Oct. 13, 2008, now U.S. Pat. No. 8,308,736, the entire contents of which are incorporated herein by reference.

TECHNICAL FIELD

The present invention relates generally to a device for delivering an intraocular lens into an eye and more particularly to fault detection in such a device.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An insertion cartridge of an IOL injector is loaded with the IOL, the tip of the insertion cartridge is inserted into the incision, and the lens is delivered into the eye.

Many IOLs manufactured today are made from a polymer with specific characteristics. These characteristics allow the lens to be folded, and when delivered into the eye, allow the lens to unfold into the proper shape. Several manual injector devices are available for implanting these lenses into the eye. However, threaded-type manual injectors require the use of two hands, which is cumbersome and tedious. Syringe-type injectors produce inconsistent injection force and displacement. Thus, improved devices and methods are needed for delivering IOLs into the eye.

SUMMARY

Embodiments of the present invention include various devices for implanting an intraocular lens (IOL) into the lens capsule of an eye, as well as methods for controlling such a device. According to an exemplary embodiment, an IOL injection device comprises a tubular housing with a plunger longitudinally disposed within the tubular housing. The plunger is longitudinally translated frontwards and rearwards, with respect to a front end of the housing, by an electric drive system disposed within the housing and comprising an electric motor. The device is configured so that when the plunger is translated towards the front of the device, its tip engages an intraocular lens insertion cartridge mounted at or near the front end of the housing. The plunger tip, which may in some embodiments be a removable plastic sleeve that snap fits to a push rod, passes through the insertion cartridge to fold and displace an intraocular lens disposed within, and to inject the folded lens into the lens capsule of an eye.

In various embodiments, the IOL injection device further comprises a control circuit, electrically connected to the electric motor and configured to start translation of the plunger, responsive to user input. The circuit is further configured to detect at least one fault condition, based on a counter-electromotive force produced by the electric motor, and to stop translation of the plunger assembly responsive to the detected fault condition. The detected fault condition may comprise excessive resistance to forward translation of the plunger, compared to a pre-determined threshold, such as might occur with an improperly loaded or otherwise occluded insertion cartridge. Some embodiments might be configured to detect excessive resistance to rearward translation of the plunger, compared to a second pre-determined threshold, and/or insufficient resistance to forward translation of the plunger, compared to a third pre-determined threshold.

In some embodiments, the control circuit is configured to monitor the rotational speed of the electric motor, based on the counter-electromotive force, and to detect at least one fault condition by comparing the monitored rotational speed to a pre-determined threshold. In some embodiments, the control circuit is configured to track the longitudinal position of the plunger, based on the counter-electromotive force produced by the electric motor, and to detect the at least one fault condition based on the tracked longitudinal position. In some of these embodiments, the control circuit is configured to detect the at least one fault condition based on comparing the counter-electromotive force produced by the electric motor to a threshold that varies with the tracked longitudinal position, such as by comparing the monitored rotational speed to a threshold that varies with the tracked longitudinal position.

In an exemplary method for controlling a device for implanting an intraocular lens in the lens capsule of an eye, wherein the device comprises a plunger longitudinally disposed inside a tubular housing and an electric drive system including an electric motor and configured to cause longitudinal translation of the plunger along a primary axis of the housing, longitudinal translation of the plunger is initiated responsive to user input. The translation of the plunger is stopped responsive to detection of at least one fault condition based on a counter-electromotive force produced by the electric motor. Detected fault conditions may include one or more of: excessive resistance to forward translation of the plunger, compared to a first pre-determined threshold; excessive resistance to rearward translation of the plunger, compared to a second pre-determined threshold; and insufficient resistance to forward translation of the plunger, compared to a third pre-determined threshold.

In some embodiments, the method may include monitoring the rotational speed of the electric motor, based on the counter-electromotive force, so that the fault condition is detected by comparing the monitored rotational speed to a pre-determined threshold. In some embodiments, the longitudinal position of the plunger is tracked, based on the counter-electromotive force, and the detection of the fault condition is based on the tracked longitudinal position. The fault condition may be detected in some embodiments by comparing the counter-electromotive force produced by the electric motor to a threshold that varies with the tracked longitudinal position, for instance by comparing a monitored rotational speed to a threshold that varies with the tracked longitudinal position.

Of course, those skilled in the art will appreciate that the present invention is not limited to the above features, advantages, contexts or examples, and will recognize additional features and advantages upon reading the following detailed description and upon viewing the accompanying drawings.

BRIEF DESCRIPTION OF THE DRAWINGS

FIG. 3 illustrates the electric drive system and coupling mechanism of an exemplary IOL injection device.

FIG. 4 illustrates a removable plunger tip according to some embodiments of the present invention.

FIG. 6 illustrates a fully retracted actuating apparatus.

FIG. 7 illustrates a partially extended actuating apparatus.

FIG. 10 illustrates a plunger tip wrench according to some embodiments of the invention.

FIG. 11 illustrates the plunger tip wrench of FIG. 10 installed on an exemplary IOL injection device.

DETAILED DESCRIPTION

Figure 1:
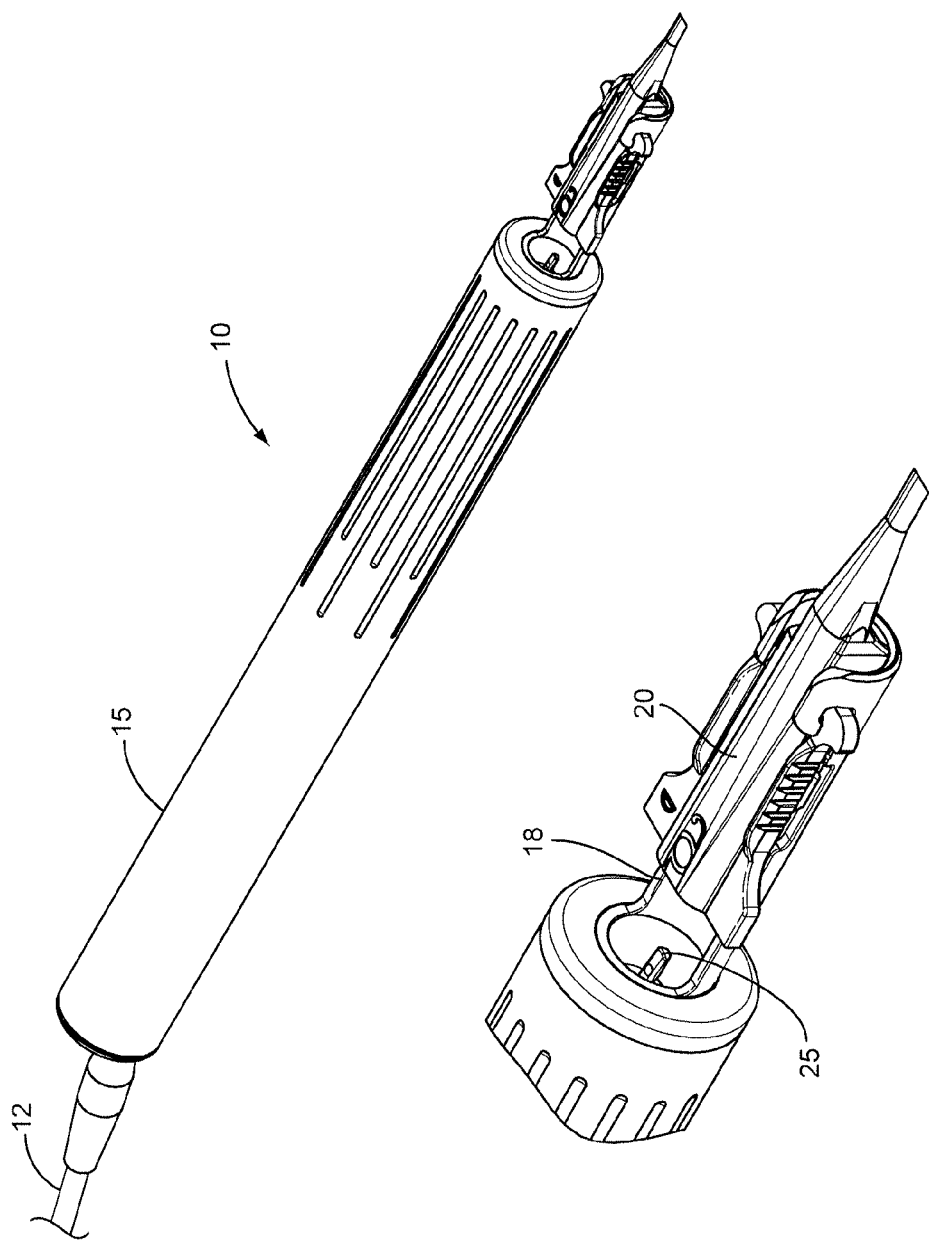
FIG. 1 is an isometric view of an exemplary IOL injection apparatus, with an insertion cartridge installed.

FIG. 1 illustrates a handheld intraocular lens (IOL) injection device 10 for implanting an IOL into the anterior capsule of the eye. As pictured, IOL injection device 10 includes a cable assembly 12 that carries power and/or control signals from a separate user console (not shown), although some embodiments may include one or more batteries in the main housing 15 to provide electrical power to the device and/or one or more switches or other user input devices to control the operation of the device. The pictured IOL injection device 10 also comprises a cartridge mount 18, which holds a removably mounted insertion cartridge 20. As will be explained in further detail below, the insertion cartridge 20 in some embodiments is a disposable polymeric component adapted to accommodate an unfolded IOL lens and to fold and displace the lens as a plunger tip 25 is translated forward from the body of the housing 15 and through the insertion cartridge 20. In some embodiments, the cartridge mount 18 may comprise a metallic "nosecone" that includes a unique cutout to accommodate the IOL cartridge and that is press-fitted to an inner shell of the housing 15.

Figure 2:
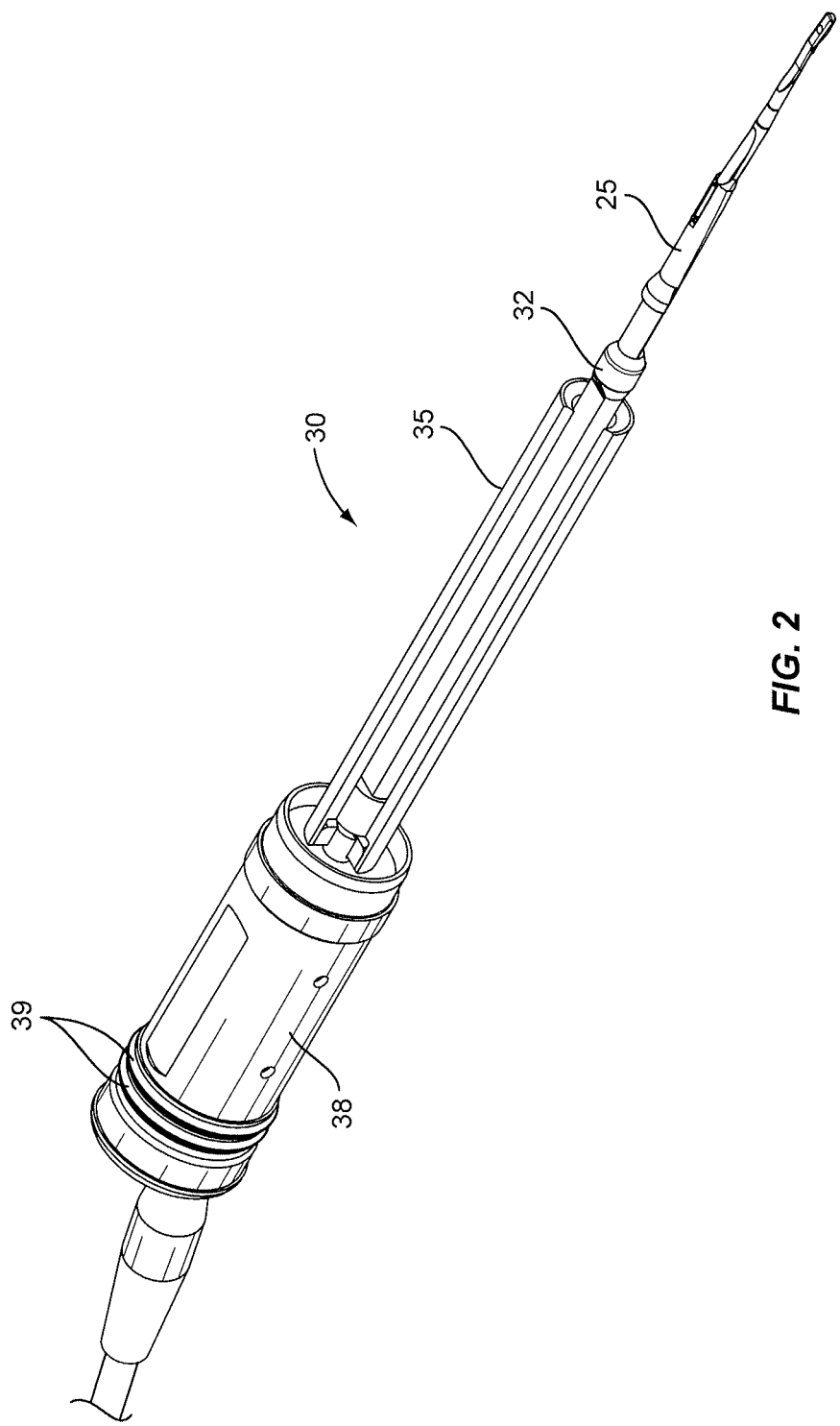
FIG. 2 is a partly cut-away isometric view of the actuating mechanism of an exemplary IOL injection device.
Figure 5:
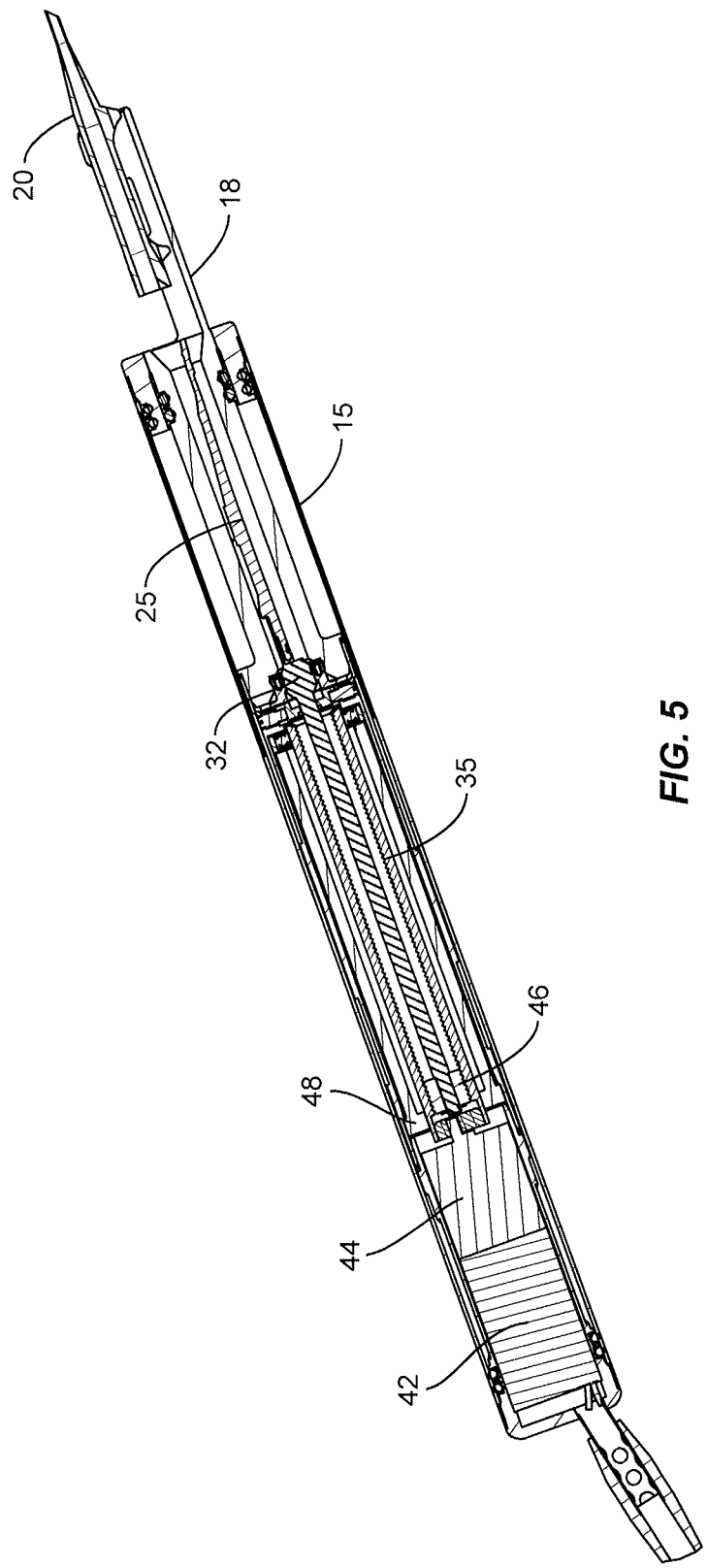
FIG. 5 is a cross-sectional view of an IOL injection device according to some embodiments of the present invention.
Figure 8:
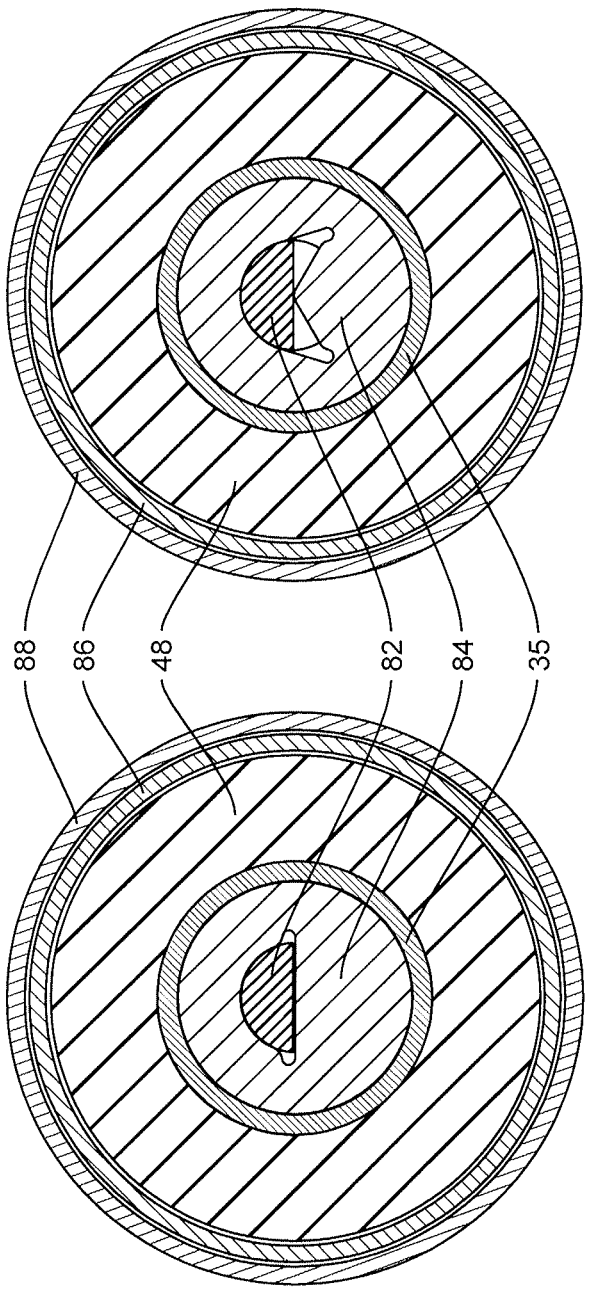
FIGS. 8A and 8B are cross-sectional views of alternative embodiments of the device of FIGS. 6 and 7, taken along line VIII.

FIG. 2 illustrates a partially cut-away view of an exemplary embodiment of IOL injection device 10, showing the internal workings of an actuating assembly 30 for linearly translating the plunger tip 25 along the primary axis of the device's housing. FIGS. 3 and 4 provide details of the assembly of FIG. 2, and FIG. 5 illustrates a cross-sectional view of the IOL injection device 10.

In the pictured embodiment, the actuating assembly comprises, in addition to the plunger tip 25, a plunger 32 configured for longitudinal translation inside an internally threaded tubular coupler 35 and an electric drive system 38. As shown in FIGS. 3 and 5, the electric drive system 38 may comprise an electric motor 42 and gear set 44 disposed within a weldment and configured to rotate the tubular coupler 35, which is held in place by a polymeric coupler sleeve 48. The internal threads on the tubular coupler 35 engage an externally threaded male coupler 46 at the rear end of the plunger 32, forcing linear translation of the plunger 32 and plunger tip 25 within the tubular coupler 35, in response to activation of the drive system 38. The internal threads of the tubular coupler 35 and/or the threads of the male coupler 46 are coated with a lubricant (which may be a dry film coating such as Endura 200TX, Brycoat WS2, Teflon/FEP, or the like) to minimize friction. O-rings 39, which may be formed from an elastomer, provide a seal to the tubular housing 15, preventing moisture and/or other contaminants from reaching the interior of the housing 15.

In some embodiments, the electric drive system 38 comprises a brushless DC motor 42 for providing rotational torque to the gear set 44, which in turn rotates the tubular coupler 35 to extend or retract the plunger 32. The gear set 44 is effective to reduce the angular velocity of the motor according to a pre-determined reduction ratio, e.g., 125:1. This increases the available torque from the drive system 38, and slows the linear motion of the plunger 32 to a speed appropriate for the IOL injection procedure.

In some embodiments, plunger tip 25 may be removable from the plunger 32, as shown in FIG. 4. In these embodiments, plunger tip 25 may comprise a disposable plastic sleeve that attaches to the forward end of the plunger 32, in some cases according to a "snap-fit" mechanism. The end of the plastic sleeve that engages the IOL is more compliant than a bare metallic plunger would be, and has a smooth surface finish, thus avoiding damage to the IOL as it is pushed through the insertion cartridge 20 and into the eye. The use of a disposable plastic sleeve may also ease re-processing of the IOL injection device 10 between uses.

FIGS. 6, 7, 8, and 9 provide additional details for an exemplary IOL injection device according to some embodiments of the present invention. FIGS. 6 and 7 illustrate a longitudinal cross-section of IOL injection device 10 with the plunger 32 in fully retracted and in partially extended positions, respectively. In the partially extended position illustrated in FIG. 7, the plunger tip 25 is just beginning to pass into the insertion cartridge 20.

As seen in FIG. 6, the male coupler 46, which is bored and "keyed" along its axis to accommodate the plunger 32, is held in place with a retaining ring 52 that clips into a circumferential groove at the rear end of the plunger 32, thus securing the male coupler 46 in place. At the opposite end of the tubular coupler 35, a bearing assembly 54, held in place by a polymeric bearing sleeve 56, holds the tubular coupler 35 in a position concentric to the housing and facilitates smooth rotational motion of the tubular coupler 35. A compression seal 58, comprising an elastomer jacket and a metal channel ring, provides a seal to prevent moisture ingress. The plunger 32, which has a cross section with two flat faces, is prevented from rotating relative to the housing by an orientation insert 60, which is held in place by pins 62.

FIGS. 8A and 8B provide cross-sectional views, corresponding to the section indicated as "VIII" in FIG. 7, of two different embodiments of IOL injection device 10. As seen in each of these figures, a drive shaft 82 extending from the gearbox 44 engages a keyed endplate 84 of tubular coupler 35 to transfer rotational torque of the drive system 38 to the tubular coupler 35. Tubular coupler 35 is surrounded by coupler sleeve 48 and an inner shell 86 and outer shell 88 of the housing 15. In the embodiment pictured in FIG. 8B, the endplate 84 of tubular coupler 35 is slotted to subtend an arc that exceeds the portion of the slot occupied by the drive shaft 82. This allows the drive shaft to rotate freely for part of a rotation upon a reversal in direction. This feature may facilitate start-up of the electric motor in some embodiments, and may also be used in some embodiments to calibrate a monitoring circuit for a "no load" condition. As will be explained in further detail below, this calibration may be used to establish one or more thresholds for use in fault detection.

Figure 9:
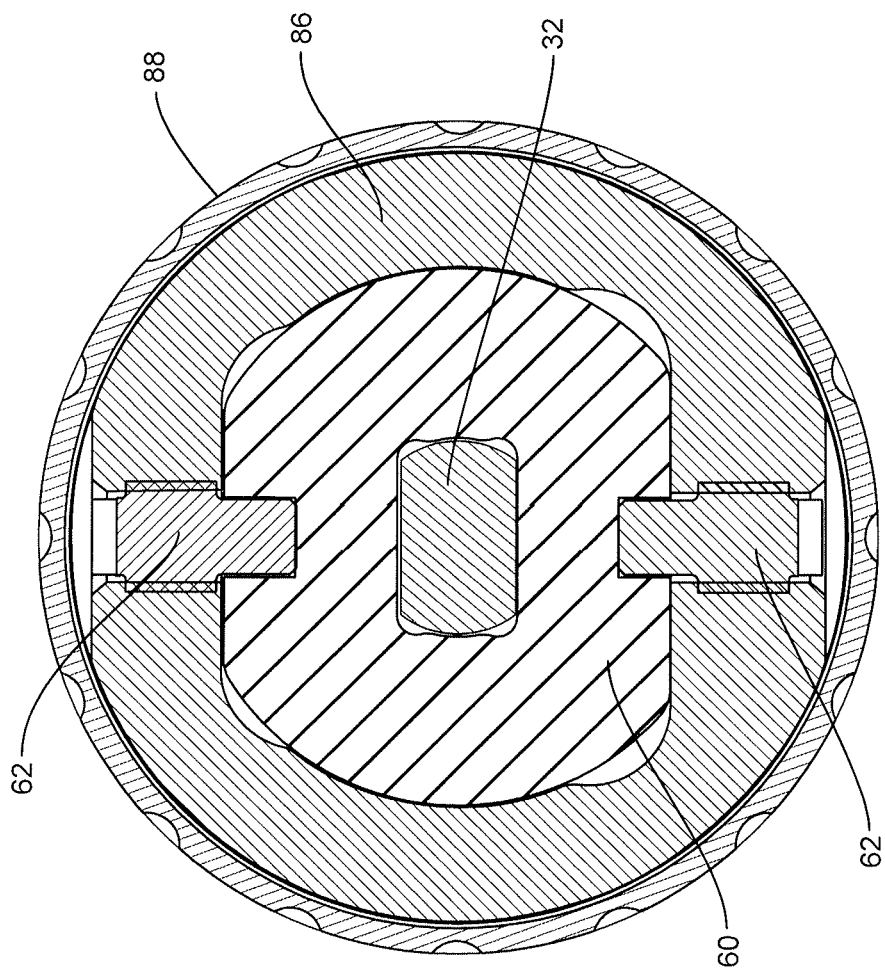
FIG. 9 is another cross sectional view of FIGS. 6 and 7, taken along line IX.

FIG. 9 provides a cross-sectional view of some embodiments of IOL injection device 10, corresponding to the section indicated as "IX" in FIG. 7. As noted above, plunger 32 has a non-circular cross section, and is held in place by orientation insert 60, which is in turn secured into position within the inner shell 86 and outer shell 88 of the housing by retaining pins 62. Because the plunger 32 is thus prevented from rotating, relative to the housing, rotation of tubular coupler 35 by the electric drive system 38 is converted into translational displacement of plunger 32 along the axis of the IOL injector device, as shown in FIGS. 6 and 7.

As shown above, in some embodiments of an IOL injector device a plunger assembly comprises two or more parts, including a push-rod 32 and a plunger tip 25. In some embodiments, plunger tip 25 may comprise a removable plastic sleeve that snap-fits onto the plunger 32, and may be disposable after use. In some embodiments, a plunger tip wrench may be used to install the plastic plunger tip 25 onto the plunger 32. FIG. 10 illustrates an exemplary plunger tip wrench 90 with a plunger tip 25 held inside. FIG. 11 shows the plunger tip wrench 90 installed onto the cartridge mount 18.

In the pictured embodiment, the plunger tip wrench 90 is secured onto the cartridge mount 18 in the same manner as the insertion cartridge 20. In some embodiments, the plunger tip 25 is automatically installed onto the plunger 32 in response to user activation of an installation mode. For example, after the user pushes an appropriate button on device or on an accompanying operator console, the plunger 32 is actuated at a default speed to snap fit the plunger into the disposable sleeve. This actuation is followed by retraction of the plunger 32 to its original starting position at a default speed. The retraction pulls the plunger tip 25 from the plunger tip wrench 90, which may then be removed and replaced with a loaded IOL insertion cartridge 20. As will be discussed in further detail below, both operations may automatically terminated responsive to monitoring of the counter-electromotive force (often called "back EMF") produced by the spinning electric motor 42.

In some embodiments in which a disposable plunger tip 25 is used, the plunger tip 25 and the insertion cartridge 20 may be provided with features so that the plunger tip 25 is automatically removed from the plunger 32 after use. In some of these embodiments, for example, the plunger tip 25 may be provided with one or more "teeth," or other protrusions, designed to engage with a corresponding catch on the insertion cartridge 20 when the end of the plunger tip 25 passes fully through the insertion cartridge 20. Once engaged, such a detention mechanism provides enough resistance to backwards movement of the plunger tip 25 so that the disposable sleeve ejects itself from the plunger. When the plunger 32 is fully retracted, the insertion cartridge 20 and the plunger tip 25 can be removed from the IOL injector as a unit, and discarded.

Figure 14A:
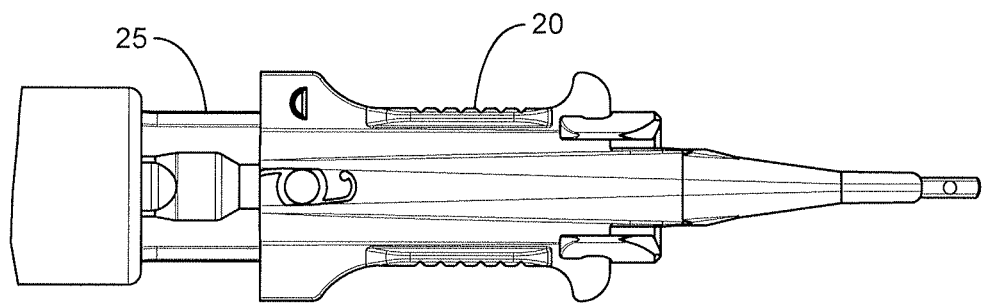
FIGS. 14A and 14B illustrate an exemplary detention feature for use with a disposable plunger tip.
Figure 14B:
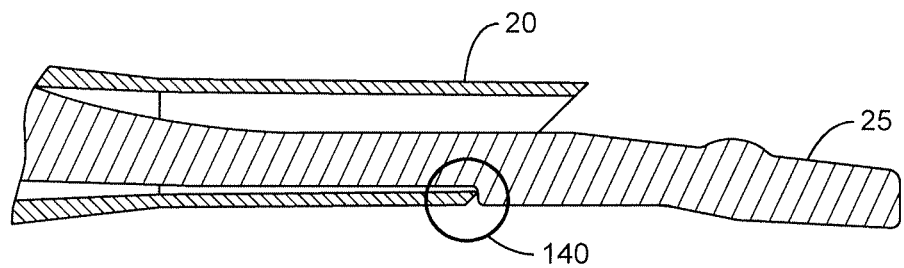

FIG. 14 illustrates an exemplary detention mechanism, as discussed above. FIG. 14A provides a top view of plunger tip 25 fully inserted into insertion cartridge 20, while FIG. 14B illustrates an exemplary detention mechanism 140, comprising mating detention features on the plunger tip 25 and insertion cartridge. In the exemplary embodiment of FIG. 14B, a protrusion from plunger tip 25 engages a lower lip of the insertion cartridge 20 when the plunger tip 25 is in its fully extended position.

Figure 12:
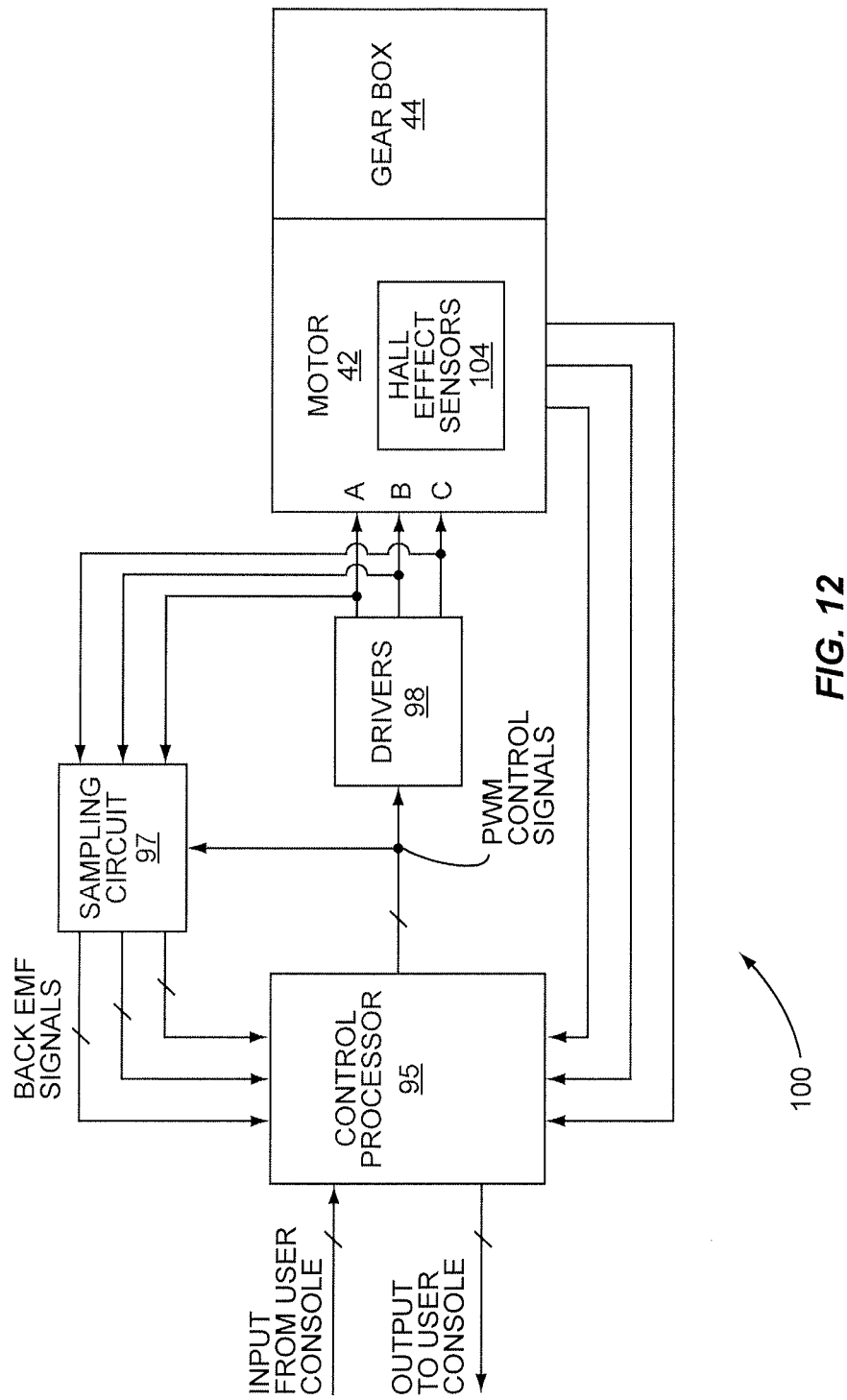
FIG. 12 is a schematic diagram illustrating an exemplary control circuit for an IOL injection device.

FIG. 12 illustrates an exemplary control circuit 100, according to some embodiments of the invention, for controlling the operation of an IOL injection device. The pictured control circuit 100 is for a three-phase, brushless DC motor 42 that includes Hall-effect sensors 104. Although not shown in FIG. 12, the motor 42 may in some embodiments provide a neutral reference point; those skilled in the art will appreciate that the presence of a neutral terminal simplifies the measurement of back EMF, but is not absolutely necessary. In any case, those skilled in the art will appreciate that the circuit of FIG. 12 may be readily adapted for motors of different types, including brushed motors. In particular, those skilled in the art will appreciate that techniques for controlling a brushless DC motor without the use of Hall-effect sensor feedback are well known.

The control circuit 100 includes a control processor 95 which produces pulse-width modulated (PWM) control signals for commutating the motor 42, as well a driver circuit 98 for converting the digital control signals into analog drive signals applied to the stator winding inputs A, B, and C. Control circuit 100 further includes a sampling circuit 97 for detecting back EMF signals from the motor's rotor inputs A, B, and C; in some embodiments, sampling circuit 97 includes analog-to-digital converters to convert the voltages at the motor inputs to digital signals for use by control processor 95. In some embodiments, sampling circuit 97 may be synchronized to the PWM control signals produced by control processor 95, so that the back EMF for a given rotor input is only sampled when the drive for that input is floating. However, those skilled in the art will appreciate that in other embodiments the motor inputs may be sampled over the entire duty cycle, and the back EMF signals isolated by digital processes in control processor 95. Those skilled in the art will appreciate that sampling circuit 97 may also include low-pass filters for each motor input signal in some embodiments, although it will be understood that the delay caused by such low-pass filters should be considered when the motor is operating at a high speed.

In the pictured embodiment, control processor 95 has access to signals from Hall-effect sensors 104; these sensor outputs provide an indication of the motor's rotor position, and may be used by control processor 95 to control the timing of the PWM signals according to conventional techniques. Alternatively, zero-crossings of the back EMF signals may be detected, with the zero-crossing times used to synchronize the PWM signals controlling the current applied to the motor. Again, techniques for starting-up and controlling a sensorless brushless motor using back EMF signals are well known. Several such techniques are described, for example, in a master's thesis entitled "Direct Back EMF Detection Method for Sensorless Brushless DC (BLDC) Motor Drives," by Jianwen Shao, Va. Polytechnic Institute and State University, Blacksburg, Va., September, 2003 (available at http://scholar.lib.vt-.edu/theses/available/etd-09152003-171904/unrestricted/T.pdf).

In some embodiments of the invention, the back EMF may also be monitored and used to detect faults in operation of the IOL injection device. For instance, due to the geometry of the intraocular lens and the volume of viscoelastic injected into the insertion cartridge, a properly loaded cartridge has a unique inherent viscous resistance to the plunger, and thus provides a known load on the motor. When compared to a loaded cartridge, the empty cartridge also has a distinct load signature. Because of the relationship between torque and speed in a DC motor, an increase in the load is reflected in a decrease in motor speed, for a given drive level. Conversely, a decrease in the load is reflected in an increase in motor speed. Because the back EMF of the motor is directly proportional to the motor's rotational speed, the level of the back EMF can be monitored to determine the motor's speed, and hence the applied load. By comparing the monitored back EMF level at a given instance to a predetermined threshold, the control processor 95 can detect whether or not the motor is operating at an expected speed. Thus, the control processor can detect faults in operation and automatically respond (e.g., by shutting down) and/or providing feedback to the user.

For example, a load cartridge containing less than the required viscoelastic in the cartridge will result in a back EMF higher than an expected level, in which case the control processor 95 can notify the user. Conversely, when the back EMF value is less than an expected level, it suggests an occluded cartridge. Again, the operation of the device can be shut down, and appropriate notice provided to the user. Of course, "normal" operation will fall within a range of back EMF levels. Thus, two separate thresholds may be used to detect excessive resistance to forward translation of the plunger and to detect insufficient resistance to translation of the plunger. (Distinct thresholds may apply to reverse translation of the plunger, in some embodiments.) The difference between these two thresholds defines the range of normal operation.

As discussed above, the magnitude of the back EMF level is directly proportional to the speed of the motor, and may be used to directly monitor the speed of the motor, and thus indirectly to monitor the load, i.e., the resistance to translation of the plunger. Alternatively, the speed of the motor may be monitored, using the back EMF, by counting zero crossings of the back EMF in a given time interval. This approach effectively counts rotations of the motor; because of the fixed relationship (defined by the gear box and the threads of the coupling mechanisms) between the motor and the linear translation, the number of motor rotations in a given time interval is directly proportional to the speed. This estimated speed may be compared, in the same manner as discussed above, to pre-determined thresholds to detect faults in operation.

In some embodiments of the present invention, counting positive-going and negative-going zero-crossing points of the back EMF provides an additional advantage, in that the longitudinal position of the plunger can be tracked at all times. Because the total number of net accumulated zero-crossing points is directly proportional to the linear translation of the plunger, the longitudinal position of the plunger within the device may be determined at any time, given only a calibrated reference point. This calibrated reference point may be defined at the time of manufacture, in some embodiments, or at the time of use in others. For example, a user may be instructed to fully retract the plunger and to then push a calibration button, setting a "zero" position for the plunger. Alternatively, a "hard stop" after retraction of the plunger can be automatically detected, using either of the methods discussed above, thus indicating the "zero" position of the plunger.

In those embodiments of the present invention that monitor the longitudinal position of the plunger, the tracked position information may be used along with the back EMF level at a given time to detect one or more fault conditions. For instance, the plunger will be engaged with the insertion cartridge only over a specific range of known lateral positions. Otherwise, e.g., as the tip of the plunger is approaching the cartridge, the plunger is expected to move with little resistance. The threshold or thresholds used to detect a fault may vary, depending on the lateral position of the plunger, to provide more accurate and/or more informative fault detection. For example, the threshold for detecting insufficient resistance to motion of the plunger may be set to a level corresponding to zero resistance for a range of lateral positions over which free movement of the plunger is expected. Over that same range, the threshold for detecting excessive resistance may be set to a level corresponding to a resistance level somewhat lower than is expected when the plunger begins to engage the insertion cartridge. For lateral positions in which the plunger is fully engaged with the cartridge, both thresholds may be adjusted to correspond to higher resistance levels.

Similarly, the threshold levels may vary with the direction of the plunger movement, and/or between two or more modes of operation. For example, a separate operational mode may be defined for installation of a removable plunger tip, in some embodiments, as was described above. In this installation mode, the fault detection thresholds may be quite different than for the normal operating mode, to account for the expected resistance when the push rod of the plunger assembly engages the plunger tip and the expected backwards resistance when the plunger tip is extracted from the plunger tip wrench.

In some embodiments of the present invention, one or more of the above-discussed thresholds is pre-determined, e.g., by factory calibration, and stored in memory in or accessible to control processor 95. (Those skilled in the art will appreciate that this memory may comprise program memory or a separate memory storing factory-determined parameters or the like, and may comprise any of several conventional memory types, including ROM, PROM, EEPROM, flash, etc.) In some embodiments, the thresholds used during operation may be adjusted relative to a "no-load" back EMF level or corresponding "no-load" rotational speed determined upon starting up the motor. As was briefly discussed, this may be facilitated by designing the drive system of the IOL injector so that it has a short interval upon each reversal in direction during which the drive system is not engaged with the plunger. One design approach is shown in FIG. 8B, and was discussed above. In such embodiments, the "no-load" level for back EMF or speed may be measured and used to establish a baseline level. This baseline level may be used to scale and/or translate stored threshold levels to obtain more accurate operational thresholds.

Figure 13:
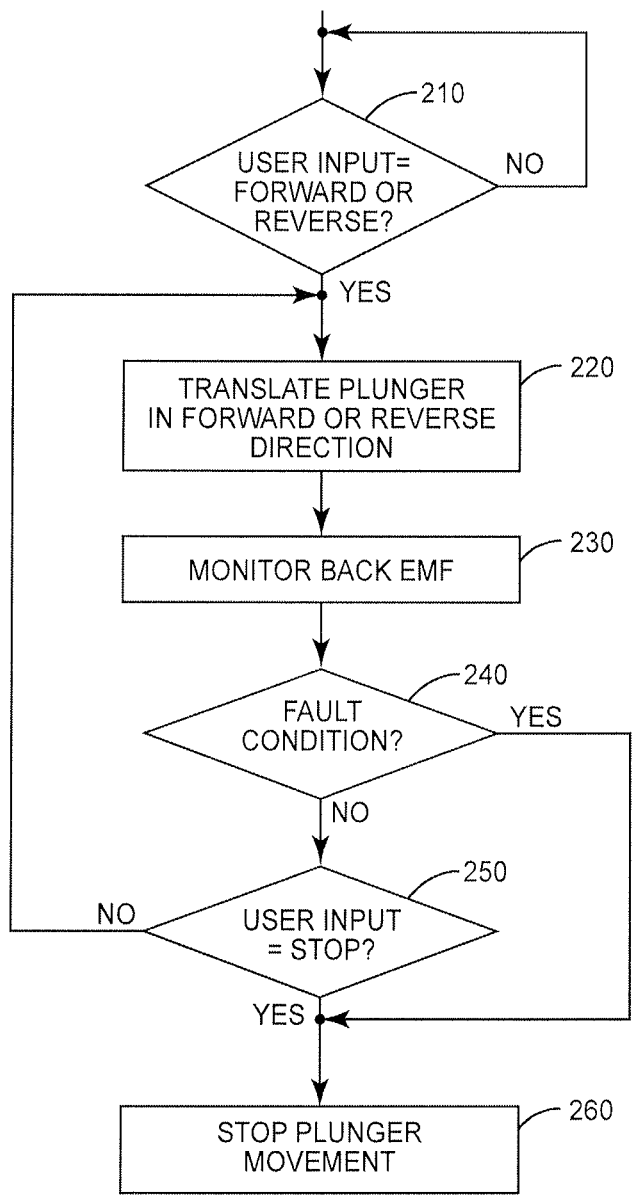
FIG. 13 is a process flow diagram illustrating a method for controlling an IOL injection device according to some embodiments of the present invention.

With the preceding discussions in mind, those skilled in the art will appreciate that the process flow diagram of FIG. 13 illustrates an exemplary embodiments of a method for controlling an intraocular lens injection device according to any of the mechanical configurations discussed above and variations thereof. Those skilled in the art will appreciate that this particular process flow is not intending to be limiting; numerous variations of this method falling within the scope of the present invention will be apparent in view of the preceding discussion. Those skilled in the art will further appreciate that the processing flow of FIG. 13 may be implemented in software or firmware stored in program memory within or associated with control processor 95, for example, which memory may comprise one or more of various conventional types including read-only memory (ROM), programmable read-only memory (PROM), flash memory, magnetic or optical memory devices, or the like.

In any case, the process flow illustrated in FIG. 13 begins with IOL injection device in an inactive state. The device checks for user input indicating that actuation of the plunger assembly should begin, as shown at block 210. This user input may originate at any of a number of conventional user input devices, such as a keypad or touchscreen at an operator console connected by cable to the IOL injection device, a foot-operated switch electrically connected to the IOL injection device by cable or via a console, or one or more switches or buttons on the body of the IOL injection device itself. In any case, in response to user input indicating that the plunger assembly should be moved, a control circuit begins translation of the plunger in the indicated direction, as shown at block 220.

As the plunger is moved, the back EMF from the electric motor is monitored, as shown at block 230, according to any of the techniques discussed above. In some embodiments, the magnitude of the back EMF level is monitored and compared to one or more pre-determined thresholds. In other embodiments, zero-crossings of the back EMF are detected and counted for a pre-determined time interval, to get an indication of the plunger's speed, and compared to one or more pre-determined thresholds. If a fault condition is detected, as indicated at block 240, the movement of the plunger is immediately suspended, as shown at block 260. As discussed above, the detected fault condition may correspond to excessive resistance to forward or backwards movement of the plunger, compared to pre-determined threshold levels, or insufficient resistance to forward or backwards movement of the plunger, compared to pre-determined threshold levels. In any of these cases, the threshold level for fault detection may vary according to a tracked longitudinal position of the plunger, as discussed earlier. Furthermore, the operational threshold levels may be adjusted according to a baseline resistance or operating speed determined during a "no-load" condition.

In some embodiments, the stopping of the plunger's movement in response to a detected fault may be accompanied with or followed by an alert to the user, indicating the fault. In some cases, a message identifying a particular type of fault (e.g., "blocked cartridge", "empty cartridge", or the like) may be provided to the user via a graphical user interface on an operator's console. If a fault condition is not detected at block 240, then the status of the user input is checked, as shown at block 250. If the user input indicates that movement of the plunger should be stopped, then the motor is deactivated and the plunger's translation is stopped, as shown at block 260. Otherwise, translation of the plunger continues, as shown at block 220, and the preceding operations are repeated until either a fault occurs or the user input indicates that the plunger assembly's movement should be stopped.

In the above discussion of the process flow of FIG. 13, it was assumed that translation of the plunger continues, once initiated, until user input directs a stop or until a fault condition is detected. Those skilled in the art that the plunger motion may be limited at either or both ends by a mechanical stop. In some embodiments, these mechanical stops may be detected by the same fault detection mechanisms as described above, i.e., by monitoring the back EMF levels and/or the speed of the motor. Alternatively, some embodiments may prevent the plunger from reaching the mechanical stops by tracking the longitudinal position of the plunger, as described above, and automatically stopping the plunger's movement before it reaches a mechanical stop.

The preceding description of various embodiments of an intraocular lens injection device and of methods for using such a device was given for purposes of illustration and example. Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A device for implanting an intraocular lens in the lens capsule of an eye, the device comprising:
   a tubular housing having a primary axis extending between front and rear ends of the housing;
   a plunger longitudinally disposed within the housing and having first and second ends, the first end being disposed towards the front end of the housing;
   an electric drive system disposed within the housing, the electric drive system including an electric motor and configured to cause longitudinal translation of the plunger along the primary axis of the housing;
   a cartridge mount at or near the front end of the housing and configured to accommodate a removable insertion cartridge in alignment with the plunger so that an intraocular lens disposed in the insertion cartridge is displaced from the insertion cartridge as the plunger is translated towards the front end of the housing;
   a control circuit, electrically connected to the electric motor and configured to start translation of the plunger responsive to user input, to detect at least one fault condition based on a counter-electromotive force produced by the electric motor, and to stop translation of the plunger responsive to the detected fault condition;
   a removable plunger tip configured to snap fit to the first end of the plunger so that the removable plunger tip engages the intraocular lens as the plunger is translated towards the front end of the housing; and
   a plunger tip wrench removably mountable to the cartridge mount and configured to accommodate the removable plunger tip for snap fitting to the first end of the plunger as the plunger is translated towards the front end of the housing and the plunger tip wrench also configured to thereafter release the removable plunger tip as the plunger is translated towards the rear end of the housing.

2. The device of claim 1, wherein the removable plunger tip comprises a first detention feature configured to engage a corresponding detention feature on the insertion cartridge when the plunger tip is fully inserted into the insertion cartridge, so that the removable plunger tip is thereafter removed from the plunger when the plunger is translated towards the rear end of the housing.

3. The device of claim 1, wherein the at least one fault condition comprises one or more fault conditions selected from the set comprising:
   excessive resistance to forward translation of the plunger, compared to a first pre-determined threshold;
   excessive resistance to rearward translation of the plunger, compared to a second pre-determined threshold; and
   insufficient resistance to forward translation of the plunger, compared to a third pre-determined threshold.

4. The device of claim 1, wherein the control circuit is configured to monitor the rotational speed of the electric motor, based on the counter-electromotive force, and to detect the at least one fault condition by comparing the monitored rotational speed to a pre-determined threshold.

5. The device of claim 1, wherein the control circuit is configured to detect the at least one fault condition based on comparing the counter-electromotive force produced by the electric motor to a threshold that varies with a longitudinal position of the plunger.

6. The device of claim 1, wherein the control circuit is configured to monitor the rotational speed of the electric motor, based on the counter-electromotive force, and to detect the at least one fault condition by comparing the monitored rotational speed to a threshold that varies with a longitudinal position of the plunger.

7. The device of claim 1, further comprising an insertion cartridge removably mountable to the cartridge mount and adapted to accommodate the intraocular lens and to fold and displace the intraocular lens from the device as the plunger is translated towards the front end of the housing.

8. The device of claim 1 further comprising a tubular coupler coupled to the electric drive system and rotatable by the electric drive system, the coupler sleeve comprising a threaded internal surfaced,
wherein the second end of the plunger comprises an outer threaded surface that matingly engages the threaded internal surface of the coupler sleeve, and
wherein the plunger is operable to longitudinally translate along the primary axis of the housing in response to rotation of the tubular coupler.

9. The device of claim 1 further comprising an orientation insert and an opening formed therein, the plunger extending through the opening,
wherein the plunger comprises a non-circular cross-section, and
wherein the opening of the orientation insert is adapted to receive the non-circular cross-section of the plunger, and
wherein the plunger and the opening cooperate to permit translation of the plunger free from rotation of the plunger relative to the housing.

10. The device of claim 1, wherein the electric drive system comprises a drive shaft comprising an end portion having semi-circular cross-section, the end portion of the drive shaft received within a slot formed within the tubular coupler,
wherein the slot defines an arc length that exceeds a size of the drive shaft, such that the drive shaft is freely rotatable within the slot relative to the tubular coupler by a defined angular amount of the arc length.

11. A device for implanting an intraocular lens in the lens capsule of an eye, the device comprising:
a tubular housing having a primary axis extending between front and rear ends of the housing;
an electric drive system disposed within the housing, the electric drive system including an electric motor;
an actuating assembly comprising:
a tubular coupler coupled to the electric drive system and rotatable by the electric drive system, the tubular coupler comprising a threaded internal surface; and
a plunger longitudinally disposed within the housing and having a first end and a second end, the first end being disposed towards the front end of the housing, and the second end comprising an outer threaded surface that matingly engages the threaded internal surface of the tubular coupler, the plunger operable to longitudinally translate along a primary axis of the housing in response to rotation of the tubular coupler;
a cartridge mount at or near the front end of the housing and configured to accommodate a removable insertion cartridge in alignment with the plunger so that an intraocular lens disposed in the insertion cartridge is displaced from the insertion cartridge as the plunger is translated towards the front end of the housing; and
a control circuit, electrically connected to the electric motor and configured to start translation of the plunger responsive to user input, to detect at least one fault condition based on a counter-electromotive force produced by the electric motor, and to stop translation of the plunger responsive to the detected fault condition.

12. The device of claim 11 further comprising an orientation insert and an opening formed therein, the plunger extending through the opening,
wherein the plunger comprises a non-circular cross-section, and
wherein the opening of the orientation insert is adapted to receive the non-circular cross-section of the plunger, and
wherein the plunger and the opening cooperate to permit translation of the plunger free from rotation of the plunger relative to the housing.

13. The device of claim 11, wherein the electric drive system comprises a drive shaft comprising an end portion having semi-circular cross-section, the end portion of the drive shaft received within a slot formed within the tubular coupler,
wherein the slot defines an arc length that exceeds a size of the drive shaft, such that the drive shaft is freely rotatable within the slot relative to the tubular coupler by a defined angular amount of the arc length.

14. The device of claim 11, wherein the at least one fault condition comprises one or more fault conditions selected from the set comprising:
excessive resistance to forward translation of the plunger, compared to a first pre-determined threshold;
excessive resistance to rearward translation of the plunger, compared to a second pre-determined threshold; and
insufficient resistance to forward translation of the plunger, compared to a third pre-determined threshold.

15. The device of claim 11, wherein the control circuit is configured to monitor the rotational speed of the electric motor, based on the counter-electromotive force, and to detect the at least one fault condition by comparing the monitored rotational speed to a pre-determined threshold.

16. The device of claim 11, wherein the control circuit is configured to detect the at least one fault condition based on comparing the counter-electromotive force produced by the electric motor to a threshold that varies with a longitudinal position of the plunger.

17. The device of claim 11, wherein the control circuit is configured to monitor the rotational speed of the electric motor, based on the counter-electromotive force, and to detect the at least one fault condition by comparing the monitored rotational speed to a threshold that varies with a longitudinal position of the plunger.

18. The device of claim 11, further comprising an insertion cartridge removably mountable to the cartridge mount and adapted to accommodate the intraocular lens and to fold and displace the intraocular lens from the device as the plunger is translated towards the front end of the housing.

19. The device of claim 11, further comprising a removable plunger tip configured to snap fit to the first end of the plunger so that the removable plunger tip engages the intraocular lens as the plunger is translated towards the front end of the housing.

20. The device of claim 19, further comprising a plunger tip wrench removably mountable to the cartridge mount and configured to accommodate the removable plunger tip for snap fitting to the first end of the plunger as the plunger is translated towards the front end of the housing and the plunger tip wrench also configured to thereafter release the removable plunger tip as the plunger is translated towards the rear end of the housing.

21. The device of claim 19, wherein the removable plunger tip comprises a first detention feature configured to engage a corresponding detention feature on the insertion cartridge when the plunger tip is fully inserted into the insertion cartridge, so that the removable plunger tip is thereafter removed from the plunger when the plunger is translated towards the rear end of the housing.

* * * * *